United States Patent [19]

Salzmann

[11] 4,152,435
[45] May 1, 1979

[54] COMPOSITIONS AND METHODS TO TREAT HYPERTENSION COMPRISING A PYRIDAZINE AND N-AMIDINO-2-(2,6-DICHLOROPHENYL) ACETAMIDE

[75] Inventor: Roland Salzmann, Ettingen, Switzerland

[73] Assignee: Sandoz Ltd., Basel, Switzerland

[21] Appl. No.: 739,658

[22] Filed: Nov. 8, 1976

[30] Foreign Application Priority Data

Nov. 13, 1975 [CH] Switzerland .................. 14718/75

[51] Int. Cl.² .................. A61K 31/165; A61K 31/495
[52] U.S. Cl. ..................................... 424/250; 424/324
[58] Field of Search ................ 424/320, 324, 326, 250

[56] References Cited

U.S. PATENT DOCUMENTS

| | | | |
|---|---|---|---|
| 3,632,645 | 1/1972 | Bream et al. | 260/558 |
| 3,838,125 | 9/1974 | Schenker | 260/250 A |
| 3,954,754 | 5/1976 | Schenker | 260/250 A |

Primary Examiner—Stanley J. Friedman
Attorney, Agent, or Firm—Gerald D. Sharkin; Robert S. Honor; Thomas O. McGovern

[57] ABSTRACT

The present invention provides a pharmaceutical composition incorporating as active agents:
  (a) a pyridazine anti-hypertensive agent, and
  (b) N-amidino-2-(2,6-dichlorophenyl)acetamide.

10 Claims, No Drawings

COMPOSITIONS AND METHODS TO TREAT HYPERTENSION COMPRISING A PYRIDAZINE AND N-AMIDINO-2-(2,6-DICHLOROPHENYL) ACETAMIDE

The present invention relates to anti-hypertensive compositions.

The present invention provides a pharmaceutical composition incorporating as active agents:
(a) a pyridazine anti-hypertensive agent, and
(b) N-amidino-2-(2,6-dichlorophenyl)acetamide.

Active agents (a) are in general known. They exhibit anti-hypertensive action by a peripheral vasodilator effect, but in general induce tachycardia.

Suitable active agents (a) may have a bicyclic nucleus containing as one fused ring a pyridazine ring, and carrying on the pyridazine ring at least one hydrazino substituent.

Such compounds include the compounds of groups (i), (ii) and (iii) below:

(i) 3-hydrazino-5,6,7,8-tetrahydropyrido[4,3-c]pyridazino derivatives, e.g., those such derivatives disclosed in formula I of D.O.S. Ser. No. 2,221,808 and D.O.S. Ser. No. 2,436,417.

Preferred active agents (a) of group (i) include those of formula I,

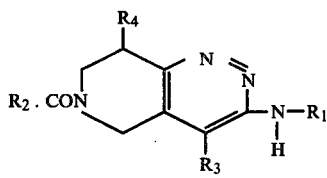

wherein $R_1$ is amino or $-N=CR_5R_6$,
wherein $R_5$ and $R_6$ are independently alkyl of 1 to 4 carbon atoms, $R_2$ is (α) alkyl or alkoxy of 1 to 6 carbon atoms,
(β) alkenyl or alkenyloxy of 3 to 6 carbon atoms, or
(γ)

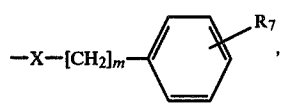

wherein X is a direct bond or oxygen,
m is 0, 1 or 2, and
$R_7$ is hydrogen, halogen of atomic number from 9 to 35, alkyl of 1 to 4 carbon atoms, or alkoxy of 1 to 4 carbon atoms, and
$R_3$ and $R_4$ are, independently, hydrogen or methyl.

Preferably any alkyl containing group has 1 or 2 carbon atoms. Conveniently when $R_2$ is alkenyl or alkenyloxy the double bond is in the β,γ-position.

Conveniently when $R_7$ is halogen, this is chlorine, especially fluroine. $R_1$ is preferably isopropylideneamino, or especially amino. $R_2$ is preferably ethoxy, phenylethyl, or phenyl or phenyl substituted by fluroine or alkoxy.

Especially preferred compounds include the following:
6-benzoyl-3-hydrazino-5,6,7,8-tetrahydropyrido[4,3-c]-pyridazine, and
3-hydrazino-5,6,7,8-tetrahydro-4,8-dimethyl-6-pyrido[4,3-c]-pyridazine carboxylic acid ethyl ester.

(ii) 3-hydrazino-cycloalkane [c]pyridazine derivatives, e.g., those such derivatives disclosed in formula I of the above mentioned D.O.S. Ser. No. 2,221,808 and D.O.S. Ser. No. 2,436,417.

Preferred active agents of group (ii) include those of formula II,

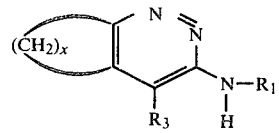

wherein
$R_1$ and $R_3$ are as defined above, and
x is 4,5 or 6.

Preferred significances for $R_1$ and $R_3$ are as mentioned above with reference to formula (I) x is preferably 5 or 6.

A preferred active agent is for example:
3-hydrazino-5,6,7,8,9,10-hexahydro-4-methylcycloocta[c]-pyridazine.

(iii) 1-hydrazinophthalazine derivatives, e.g., 1-hydrazinophthalazine, 1-[2-(1,3-dimethyl-2-butenylidene)-hydrazino]phthalazine, 1,4-dihydrazinophthalazine or 1-(N'-ethoxycarbonylhydrazino)phthalazine.

The peripheral vasodilator and tachycardia effects exhibited by active agents (a) may be observed in standard animal tests. For example, the effects may be observed in the conscious, spontaneous hypertonic rat test, wherein a catheter is implanted in the rat aorta according to the principles of Weeks et al., Proc. Soc. Exp. Biol. Med. 104, 646-648 (1960) and McIlreath et al., Arch. Int. Pharmacodyn. 157, 330-338 (1965).

It has now been surprisingly found that combination of active agents (a) and (b) results in advantageous anti-hypertensive activity involving reduced tachycardia when active agent (a) is administered i.p. at a dose of from 0.01 to 10 mg/kg animal body weight and active agent (b) is administered i.p. concomitantly at a dose of from about 0.01 to about 10 mg/kg animal body weight.

The combination of active agents (a) and (b) is therefore especially useful as an anti-hypertensive preparation.

The dosage and weight ratio of (a) and (b) will, of course, vary depending on the compounds employed, mode of administration and therapy desired. However, in general, satisfactory results are obtained when administered at a daily dosage of active agent (a) of from 0.01 mg to about 10 mg per kg animal body weight. For the larger mammal, the total daily dosage is in the range from about 1 to about 50 mg, preferably 2 to 30 mg.

An indicated weight ratio of active agent (a) to active agent (b) (based on the weight of the free base forms) is from 15:1 to 1:10 e.g., from 10:1 or 9:1 to 1:1, 3:7 or 1:9. A preferred weight ratio is from 10:1 to 2:1, especially 5:1; 2.5:1 or 2:1.

The daily dosage may be conveniently administered 2 to 4 times a day, preferably 3 times a day, in divided doses, conveniently in unit dosage form, or in sustained release form.

Active agents (a) and (b) may be combined in one dosage form or retained separately until required for concomitant administration. Preferred weights of active agent (a) in a unit dosage form are for example, 2 mg, 2.5 mg, 5 mg or 10 mg.

The present invention also provides a twin pack one portion thereof containing active agent (a) and another portion thereof containing active agent (b).

The present invention also provides a pack containing active agents (a) and (b) in physical relation to instructions for the concomitant administration of an antihypertensive amount of active agents (a) and (b).

The present invention also provides a process for the production of a pharmaceutical composition as defined above including the step of bringing together active agents (a) and (b).

Processes used for the formulation of such pharmaceutical compositions are known in the art, e.g., as described in the Examples hereinafter. Pharmaceutical compositions containing active agents (a) and (b) separately are in general known. Pharmaceutical compositions containing both active agents (a) and (b) may be formulated using the same principles so as to be suitable for enteral or parenteral administration.

Depending on the compound used and composition contemplated the active agent (a) and/or active agent (b) may be in pharmaceutically acceptable acid addition salt form. Such forms are known and may be made from the free base form in conventional manner. Suitable salts for active agent (a) include the hydrochloride. Suitable salts for active agent (b) include the hydrochloride, methanesulphonate, sulphate and fumarate.

Tablets, capsules, dragées, suppositories,—suspensions and sirups—may be used for enteral administration. Injectable suspensions or solutions may be used for parenteral administration. Preferably both active agent (a) and active agent (b) are administered orally, in the form of a unit dosage. Such a unit dosage may, if desired, have the active agents (a) and (b) separately encompassed therein, e.g., in separate layers in a mantle tablet.

Aside from the active agents the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweetening substances, etc. Adjuvants for the production of tablets may be, e.g., calcium carbonate, lactose, micro-crystalline cellulose, mannitol, or talc. Starch and alginic acid or micro-crystalline cellulose may be used as granulating and disintegrating agents, starch, polyvinylpyrrolidone and gelatine may be used as binding agents, and magnesium stearate, stearic acid, colloidal silica and talc as lubricants. Tablet formulations may be coated or uncoated, with the coating being applied in a manner per se and having the purpose of delaying the disintegration and adsorption in the gastrointestinal tract, thus providing a retarded effect over a longer period. Suitable suspending agents for the production of liquid administration forms are, e.g., methyl cellulose, and sodium alginate. Suitable wetting agents are, e.g., polyoxyethylene stearate and polyoxyethylene sorbitan-monooleate. Furthermore, preservatives such as p-hydroxy-benzoic acid alkyl ester may be used. Capsule formulations may contain the active agents (a) and (b) on their own or together with an inert solid diluent, for example calcium phosphate, calcium sulphate, corn starch, lactose, mannitol, colloidal silica, magnesium stearate, and micro-crystalline cellulose.

Solid preparations are preferred, especially for active agent (a), e.g., hard-gelatine capsules and tablets.

Insofar as the production of any compound or pharmaceutical composition is not particularly described herein, these may be made in known manner or analogous to known processes or analogous to processes described herein.

The following Examples are illustrative of compositions.

EXAMPLE 1

Pack containing active agents (a) and (b) separately.

Active agent (a)

165 mg capsules having either of the following compositions are used:

| Constituent | Weight mg | mg |
|---|---|---|
| (i) 6-benzoyl-3-hydrazino-5,6,7,8-tetrahydropyrido[4,3-c]pyridazine methane sulphonate | 6.785 | 13.57+ |
| (ii) CaSO$_4$ . 2H$_2$O | 81.215 | 74.43 |
| (iii) Corn starch (partially dried) | 75 | 75 |
| (iv) Colloidal silica | 1.0 | 1.0 |
| (v) Magnesium stearate | 1.0 | 1.0 |

+6.785 mg = 5 mg base

The capsules are formulated in the following way: To constituent (i) is added in turn constituent (ii), constituent (iii), constituent (iv) and constituent (v), with mixing and sieving (hole diameter 0.31 to 0.35 mm) after each new constituent is added. After the final sieving the resultant mass is processed into hard gelatine capsules in conventional manner.

Active agent (b)

55 mg tablets having the following composition are used:

| Constituent | Weight (mg) |
|---|---|
| (i) N-amidino-2-(2,6-dichlorophenyl)-acetamide | 1.15 (= 1 mg base) |
| (ii) Lactose | 45.20 |
| (iii) Micro-crystalline | 5.85 |
| (iv) Polyvinylpyrrolidone | 1.9 |
| (v) Stearic acid | 0.9 |

The tablets are formulated as follows:

0.115 kg of constituent (i) is mixed with 1.5 kg of constituent (ii) and sieved (hole diameter 0.35 mm). 1.5 kg of constituent (ii) is added to the sieved mixture and after further mixing sieving is carried out as before. 1.52 kg of constituent (ii) and 0.31 kg of constituent (iii) are added. After further mixing the mass is kneaded for 10 minutes. 0.19 kg of constituent (iv) is added and the mass is wetted with 850 g of isopropanol. Kneading and granulation is carried out with drying of the mass initially at 35° C. for 10 minutes and then at 45°–50° C. for 2½ hours. After sieving (hole diameter 0.35 mm), 0.275 kg of constituent (iii) as well as 0.09 kg of constituent (v) is added. The resultant mass is formed into tablets of 5 mm diameter.

EXAMPLE 2

Tablets and capsules containing active agents (a) and (b) in combination

Tablets and capsules comprising the following constituents may be made in analogous manner to that described in Example 1:

| Constituent | Weight (mg) | |
|---|---|---|
| (i) 6-benzoyl-3-hydrazino-5,6,7,8-tetra-hydropyrido[4,3-c]pyridazine methane sulphonate | 6.875 | (= 5 mg base) |
| (ii) N-amidino-2-(2,6-dichlorophenyl)-acetamide | 2.3 | (= 2 mg base) |
| (iii) Lactose | 90.8 | |
| (iv) Corn starch | 12.9 | |
| (v) Polyvinylpyrrolidone | 4.8 | |
| (vi) Talc | 1.125 | |
| (vii) Magnesium stearate | 1.2 | |

EXAMPLE 3

Active agent (a) given in Example 1 and/or 2 may be replaced by any other active agent (a) mentioned hereinbefore.

I claim:

1. A pharmaceutical composition useful in the treatment of hypertension comprising a therpeutically effective amount of active agents:
   (a) a 6-benzoyl-3-hydrazino-5,6,7,8-tetrahydropyrido[4,3-c]pyridazine, and
   (b) N-amidino-2-(2,6-dichlorophenyl)-acetamide, in a ratio of active agent (a) to active agent (b) of from 15:1 to 2:1, and a pharmaceutically acceptable carrier therefor.

2. A pharmaceutical composition according to claim 1, wherein the ratio of active agent (a) to active agent (b) is 10:1 to 2:1.

3. A pharmaceutical composition according to claim 1, wherein the weight ratio of active agent (a) to active agent (b) is 5:1.

4. A pharmaceutical composition according to claim 1, wherein the weight ratio of active agent (a) to active agent (b) is 2.5:1.

5. A pharmaceutical composition according to claim 1, wherein the weight ratio of active agent (a) to active agent (b) is 2:1.

6. A method of treating hypertension in animals which comprises administering to said animals concomitantly an antihypertensive effective amount of active agents:
   (a) 6-benzoyl-3-hydrazino-5,6,7,8-tetrahydropyrido[4,3-c]pyridazine, and
   (b) N-amidino-2-(2,6-dichlorophenyl)-acetamide, in a ratio of active agent (a) to active agent (b) of from 15:1 to 2:1, and a pharmaceutically acceptable carrier therefor.

7. A method according to claim 6 wherein the ratio of active agent (a) to active agent (b) is from 10:1 to 2:1.

8. A method according to claim 6, wherein the weight ratio of active agent (a) to active agent (b) is 5:1.

9. A method according to claim 6, wherein the weight ratio of active agent (a) to active agent (b) is 2.5:1.

10. A method according to claim 6, wherein the weight ratio of active agent (a) to active agent (b) is 2:1.

UNITED STATES PATENT AND TRADEMARK OFFICE
CERTIFICATE OF CORRECTION

PATENT NO. : 4,152,435
DATED : May 1, 1979
INVENTOR(S) : Roland Salzmann

It is certified that error appears in the above-identified patent and that said Letters Patent are hereby corrected as shown below:

Column 4, line 48, after the word "crystalline" insert the word --cellulose--.

Claim 1, line 31, after the term "(a)" and before the number "6" (first occurrence) delete the letter "a".

Claim 6, lines 23 and 24, delete the phrase "and a pharmaceutically acceptable carrier therefor".

Signed and Sealed this

Twenty-ninth Day of January 1980

[SEAL]

Attest:

SIDNEY A. DIAMOND

Attesting Officer

Commissioner of Patents and Trademarks